US007638486B2

(12) United States Patent
Lazarov et al.

(10) Patent No.: US 7,638,486 B2
(45) Date of Patent: Dec. 29, 2009

(54) METHOD FOR PROMOTING HARD TISSUE FORMATION

(75) Inventors: Mirella Lazarov, Hayward, CA (US); Catherine Middleton-Hardie, Hayward, CA (US); David Rosen, Hayward, CA (US)

(73) Assignee: Acologix, Inc., Hayward, CA (US)

( * ) Notice: Subject to any disclaimer, the term of this patent is extended or adjusted under 35 U.S.C. 154(b) by 317 days.

(21) Appl. No.: 11/457,091

(22) Filed: Jul. 12, 2006

(65) Prior Publication Data

US 2008/0096798 A1    Apr. 24, 2008

Related U.S. Application Data

(60) Provisional application No. 60/805,201, filed on Jun. 19, 2006, provisional application No. 60/803,327, filed on May 26, 2006, provisional application No. 60/747,255, filed on May 15, 2006, provisional application No. 60/747,143, filed on May 12, 2006, provisional application No. 60/700,518, filed on Jul. 18, 2005.

(51) Int. Cl.
*A61K 38/18* (2006.01)
*C07K 14/51* (2006.01)
*A61F 2/00* (2006.01)

(52) U.S. Cl. .................. 514/2; 530/399; 424/422

(58) Field of Classification Search ............ None
See application file for complete search history.

(56) References Cited

U.S. PATENT DOCUMENTS

| | | | |
|---|---|---|---|
| 5,015,628 A | 5/1991 | Reynolds | |
| 5,407,644 A | 4/1995 | Rytter et al. | |
| 5,837,674 A | 11/1998 | Kumagai et al. | |
| 5,846,931 A | 12/1998 | Hattersley et al. | |
| 5,849,865 A | 12/1998 | Cheng et al. | |
| 6,027,592 A | 2/2000 | Tseng et al. | |
| 6,045,780 A | 4/2000 | Bixler et al. | |
| 6,145,655 A | 11/2000 | Ruben | |
| 6,300,062 B1 | 10/2001 | Cerny et al. | |
| 6,329,357 B1 | 12/2001 | Norman et al. | |
| 6,673,900 B2 | 1/2004 | Rowe | |
| 6,790,639 B2 | 9/2004 | Brown et al. | |
| 6,911,425 B2 | 6/2005 | Kumagai et al. | |
| 7,271,151 B2 * | 9/2007 | Rowe | 514/12 |
| 2002/0102641 A1 | 8/2002 | Schia Vi et al. | |
| 2002/0197267 A1 | 12/2002 | Kumagai et al. | |
| 2003/0166239 A1 | 9/2003 | Brown et al. | |
| 2004/0126375 A1 * | 7/2004 | Langenfeld | 424/145.1 |
| 2004/0230310 A1 * | 11/2004 | Ferree | 623/17.16 |

FOREIGN PATENT DOCUMENTS

| | | |
|---|---|---|
| EP | 1 820 522 A1 | 8/2007 |
| JP | 4-74132 | 3/1992 |
| JP | 4-506511 | 11/1992 |
| JP | 11-506672 | 6/1999 |
| JP | 11-318498 | 11/1999 |
| JP | 2002-500898 | 1/2002 |
| JP | 2002-512018 | 4/2002 |
| WO | WO 95/14714 A | 6/1995 |
| WO | WO 99/08730 A | 2/1999 |
| WO | WO 99/48909 | 2/1999 |
| WO | WO 99/43844 | 9/1999 |
| WO | WO 99/48909 A2 | 9/1999 |
| WO | WO 99/60017 A2 | 11/1999 |
| WO | WO 00/52041 | 9/2000 |
| WO | WO 01/72826 | 10/2001 |
| WO | WO 02/05836 A | 1/2002 |
| WO | WO03/027246 | 4/2003 |
| WO | WO 03/066666 | 8/2003 |
| WO | WO 2006/078464 | 7/2006 |

OTHER PUBLICATIONS

Abe et al., "Differentiation of mouse myeloid leukemia cells induced by 1α,25-dihydroxyvitamine D3" *PNAS*, 78(8):4990-4994 (1981).
Bairoch et al. (1990) "EF-hand motifs in inositol phospholipid-specific phospholipase C." *FEBS*, vol. 269(2):454-456.
Bikle, "Vitamin D: New Actions, New Analogs, New Therapeutic Potential; Update 1995" *Endocrine Review*, 4(1):77-83 (1995).
Brenza et al., "Parathyroid hormone activation of the 25-hydroxyvitamine D3-1α-Hydroxylase gene promoter" *PNAS* 95:1387-1391 (1998).
Carpenter, "New Perspectives on the Biology and Treatment of X-Linked Hypophsphatemic Rickets" *Pediatric Endocrinology* 44(2):443-465 (1997).
Carswell, "The Potential for Treating Neurodegenerative Disorders with NGF-Inducing Compounds" *Experimental Neurology*, 124:36-42 (1993).
Chappard et al., (1995) "Effects of tiludronate on bone loss in paraplegic patients." *Journal of Bone and Mineral Research*, 10(1):112-118.
Chauvaux et al. (1990) "Calcium-binding affinity and calcium-enhanced activity of Clostridium thermocellum endoglucanase D." *Biochem. J.*, vol. 265:261-265.
Davis (1990) "The many Faces of Epidermal Growth Factor Repeats." *The New Biologist*, vol. 2(5):410-419.
Ecarot et al., "Defective Bone Formation by Hyp Mouse Bone Cells Transplanted into Normal Mice: Evidence in Favor of an Intrinsic Osteoblast Defect" *Journal of Bone and Mineral Research*, 7:215-200 (1992).

(Continued)

*Primary Examiner*—Marianne P Allen
*Assistant Examiner*—Regina M DeBerry
(74) *Attorney, Agent, or Firm*—Karl Bozicevic; Bozicevic, Field & Francis LLP

(57) ABSTRACT

Formulations and methods to promote biological processes to form or regenerate new hard tissues such as bones, cartilage, and/or dental tissues are disclosed. The formulation comprising two proteins is administered to enhance biological activities of a hard tissue growth and differentiation factor characterized by specific and selective upregulation and/or extension of the retention time of the intracellular enzymes and signaling molecules that play important roles to proliferate, differentiate, maturate, and/or mineralize the hard tissue forming cells.

5 Claims, 5 Drawing Sheets

OTHER PUBLICATIONS

Ecarot et al., "Effect of 1,25-Dihydroxyvitamin D3 Treatment on Bone Formation by Transplanted Cells from Normal and X-Linked Hypophosphatemic Mice" *Journal of Bone and Mineral Research*, 10:424-431 (1995).

Economou et al. (1990) "The Rhizobium nodulation gene nodO encodes a $Ca^{2+}$-binding protein that is exported without N-terminal cleavage and is homologous to haemolysin and related proteins." *The EMBO Journal*, vol. 9(2):349-354.

Eto et al., "Assay of 25-Hydroxyvitamin D3 1 α-Hydroxylase in Rat Kidney Mitochondria" *Analytical Biochemistry*, 258:53-58 (1998).

Ferris D. M. et al., "RGD-coated titanium implants stimulate increased bone formation in vivo" Biomaterials, Vo. 20, No. 23-24, Dec. 1999. pp. 2323-2331.

Fisher et al., "Inhibition of Osteoclastic Bone Resorption in Vivo by Eschistatin an "Arginyol-Glycyl-Aspartyl" (RGD)-Containing Protein" *Endocrinology*, 132(3):1411-1413 (1993).

Fratzl et al., (1994) "Abnormal bone mineralization after fluoride treatment in osteoporosis: a small-angle x-ray-scattering study." *Journal of Bone and Mineral Research*, 9(10):1541-1549.

Gennari et al., (1994) "Management of osteoporosis and Paget's disease. An appraisal of the risks and benefits of drug treatment." *Drug. Saf.*, 11(3):179-95.

George et al., "Characterization of a Novel Dentin Matrix Acidic Phosphoprotein" *The Journal of Biological Chemistry*, 268 (17):12624-12630 (1993).

Gronowicz et al., (1994) "Synthetic peptide containing Arg-Gly-Asp inhibits bone formation and resorption in a mineralizing organ culture system of fetal rat parietal bones." *Journal of Bone and Mineral Research*, 9(2):193-201.

Hayashibara T. et al., "A synthetic peptide fragment of human MEPE stimulates new bone formation in vitro and in vivo" Journal of Bone and Mineral Research, New York, NY., US, vol. 19, No. 3, Mar. 2004, pp. 455-462.

Hewison et al., "1α-Hydroxylase and the action of vitamin D" *Journal of Molecular Endocrinology*, 25:141-148 (2000).

Hilfiker, (1998) "Characterization of a murine type II sodium-phosphate cotransporter expressed in mammalian small intestine." *Proc. Natl. Acad. Sci. USA*, 95(24):14564-14569.

Horton et al., "Arg-Gly-Asp (RGD) Peptides and the Anti-Vitronectin Receptor Antibody 23C6 Inhibit Dentine Resorption and Cell Spreading by Osteoclasts" *Experimental Cell Research*, 195:368-375 (1991).

Inomata et al., "Effect of 1α(OH)-vitamin D3 on insulin secretion in diabetes mellitus" *Bone and Mineral*, 1:187-192 (1986).

Kato et al., "Molecular Genetics of Vitamin D-Dependent Hereditary Rickets" *Hormone Research*, 57:73-78 (2002).

Kawasaki et al. (1995) "Calcium-Binding Proteins 1: EF-hands." *Protein Profile*, vol. 2(4):305-356.

Kimmel-Jehan et al., "Cloning of the mouse 25-hydroxyvitamin D3-1α-hydroxylase (CYP1α) gene" *Biochimica et Biophysica Acta*, 1475:109-113 (2000).

Lajeunesse et al., "Direct demonstration of a humorally-mediated inhibition of renal phosphate transport in the Hyp mouse" *Kidney International* 50:1531-1538 (1996).

Lopez-Moratalla et al., "A common structural motif in immunopotentiating peptides with sequences present in human autoantigens. Elicitation of a response mediated by monocytes and Th1 cells" Biochimica et Biophysica Acta, vol. 1317, No. 3, 1996, pp. 183-191.

Lufkin et al., (1994) "Pamidronate: an unrecognized problem in gastrointestinal tolerability." *Osteoporos. Int.*, 4(6):320-322.

Martin et al., "Strategies to Minimize Bone Disease in Renal Failure" *American Journal of Kidney Diseases*, 38(6):1430-1436 (2001).

Meyer et al., "The Renal Phosphate Transport Defect in Normal Mice Parabiosed to X-Linked Hypophosphatemic Mice Persists After Parathyroidectomy" *Journal of Bone and Mineral Research*, 4(4):523-532 (1989).

Meyer et al., "Parabiosis Suggests a Humoral Factor Is Involved in X-Linked Hypophsphatemia in Mice" *Journal of Bone and Mineral Research*, 4(4):493-500 (1989).

Miller et al., "Genetics of vitamin D biosynthesis and its disorders" *Best Practice & Research Clinical Endocrinology and Metabolism*, 15(1):95-109 (2001).

Moncrief et al. (1990) "Evolution of EF-Hand Calcium-Modulated Proteins. I. Relationships Based on Amino Acid Sequences." *J. Mol. Evol.*, vol. 30:522-562.

Morgan et al., "Renal Transplantation in Hypophsphatemia With Vitamin D-Resistant Rickets" *Arch. Intern. Med.*, 134:549-552 (1974).

Muller et al., "1α,25-Dihydroxyvitamin D3 and a novel vitamin D analogue MC 903 are potent inhibitors of human interleukin 1 in vitro" *Immunology Letters*, 17:361-366 (1988).

Mundy et al., (1999) "Stimulation of bone formation in vitro and in rodents by statins." *Science*, 286:1946-1949.

Nesbitt et al., "Crosstransplantation of Kidneys in Normal and Hyp Mice" *J. Clin. Invest.* 89:1453-1459 (1992).

Nesbitt et al., "Phosphate Transport in Immortalized Cell Cultures from the Renal Proximal Tubule of Normal and Hyp Mice: Evidence That the HYP Gene Locus Product Is an Extrarenal Factor" *Journal of Bone and Mineral Resesarch*, 10(9):1327-1333 (1995).

Nesbitt et al., "Normal Phosphate Transport in Cells from the S2 and S3 Segments of *Hyp*-Mouse Proximal Renal Tubules" *Endocrinology*, 137(3):943-948 (1996).

Nesbitt et al., "Abnormal Parathyroid Hormone-Realted Peptide Formulation of Renal 25-Hydroxyvitamin D-1-Hydroxylase In Hyp Mice: Evidence for a Generalized Defect of Enzyme Activity in the Proximal Convoluted Tubule" *Endocrinology*, 127(2):843-848 (1990).

Petersen et al., "Identification of Osteoblast/Osteocyte Factor 45 (OF45), a Bone-specific cDNA Encoding an RGD-containing Protein That Is Highly Expressed in Osteoblasts and Osteocytes" *The Journal of Biological Chemistry*, 275(46):36172-36180 (2000).

Qiu et al., "Parental origin of mutant allele does not explain absence of gene dose in X-linked *Hyp* mice" *Gene Res. Camb.*, 62:39-43 (1993).

Rowe et al., "Distribution of mutations in the PEX gene in families with X-linked hypophosphataemic rickets (HYP)" *Human Molecular Genetics* 6(4):539-549 (1997).

Rowe, "The role of the PHEX gene (PEX) in families with X-linkd hypophosphataemic rickets" *Curr. Opin. Nephrol. Hypertens.*, 7:367-376 (1998).

Rowe, "The PEXGene: Its Role in X-Linked Rickets, Osteomalacia, and Bone Mineral Metabolism" *Experimental Nephrology*, 5:355-363 (1997).

Rowe et al., "Candidate 56 and 58 kDa Protein(s) Responsible for Mediating the Renal Defects in Oncogenic Hypophosphatemic Osteomalacia" *Bone*, 18(2):159-169 (1996).

Rowe et al., (2000) "MEPE, a new gene expressed in bone marrow and tumors causing osteomalacia." *Genomics*, 67:54-68.

Rowe et al., (2004) "MEPE has the properties of an osteoblastic phosphatonin and minhibin" 34:303-319.

Schafer et al. (1995) "Isolation of a YAC Clone Covering a Cluster of Nine S100 Genes on Human Chromosome 1q21: Rationale for a New Nomenclature of the S100 Calcium-Binding Protein Family." *Genomics*, vol. 25:638-643.

Schneider et al., (1995) "Does HRT modify risk of gynecological cancers?" *Int. J. Fertil. Menopausal Study*, 40(1):40-53.

Springer et al. (2000) "A Novel $Ca^{2+}$ Binding β Hairpin Loop Better Resembles Integrin Sequence Motifs than the EF Hand." *Cell*, vol. 102:275-377.

Stubbs et al., "Characterization of Native and Recombinant Bone Sialoprotein: Delineation of the Mineral-Binding and Cell Adhesion Domains and Structural Analysis of the RGD Domain" *Journal of Bone and Mineral Research*, 12(8):1210-1222 (1997).

Takeyama et al., "25-Hydroxyvitamin D3 1α-Hydroxylase and Vitamin D Synthesis" *Science*, 277:1827-1830 (1997).

Traianedes et al., (1998) "5-Lipoxygenase metabolites inhibit bone formation in vitro." *Endocrinology*, 139:3178-3184.

Yang et al., "Peptide analogs from E-cadherin with different calcium-binding affinities" *J. Peptide Res.*, 55:203-215 (2000).

Yoshida et al., "Identification of a Renal Proximal Tubular Cell-Specific Enhancer in the Mouse 25-Hydroxyvitamin D 1α-Hydroxylase Gene" *J. Am. Soc. Nephrol.*, 13:1455-1463 (2002).

Yoshida et al., "Mediation of Unusually High Concentrations of 1,25-Dihydroxyvitamin D in Homozygous *klotho* Mutant Mice by Increased Expression of Renal 1α-Hydroxylase Gene" *Endocrinology*, 143(2):683-689 (2002).

Zehnder et al., "Extrarenal Expression of 25-Hydroxyvitamin $D_3$-1α-Hydroxylase" J. Clin. Endocrinol. Metab., 86(2):888-894 (2001).

Zoidis et al., "Phex cDNA cloning from rat bone and studies on Phex mRNA expression: tissue-specificity, age-dependency, and regulation by insulin-like growth factor (IGF) I in vivo" *Molecular and Cellular Endocrinology*, 168:41-51 (2000).

* cited by examiner

SEQUENCE LISTING

```
<160> NUMBER OF SEQ ID NOS: 8

<210> SEQ ID NO 1
<211> LENGTH: 10
<212> TYPE: PRT
<213> ORGANISM: H. sapiens
<220> FEATURE:
<221> NAME/KEY: VARIANT
<222> LOCATION: (6)...(6)
<223> OTHER INFORMATION: Xaa can be from 1 to 10 amino acids long
<220> FEATURE:
<221> NAME/KEY: VARIANT
<222> LOCATION: 4, 6, 9
<223> OTHER INFORMATION: Xaa = Any Amino Acid

<400> SEQUENCE: 1

Arg Gly Asp Xaa Asp Xaa Ser Gly Xaa Gly
1               5                   10

<210> SEQ ID NO 2
<211> LENGTH: 10
<212> TYPE: PRT
```

```
<213> ORGANISM: H. sapiens
<220> FEATURE:
<221> NAME/KEY: VARIANT
<222> LOCATION: (6)...(6)
<223> OTHER INFORMATION: Xaa can be from 1 to 10 amino acids long
<220> FEATURE:
<221> NAME/KEY: VARIANT
<222> LOCATION: 6, 9
<223> OTHER INFORMATION: Xaa = Any Amino Acid

<400> SEQUENCE: 2

Arg Gly Asp Asn Asp Xaa Ser Gly Xaa Gly
1               5                  10

<210> SEQ ID NO 3
<211> LENGTH: 10
<212> TYPE: PRT
<213> ORGANISM: H. sapiens
<220> FEATURE:
<221> NAME/KEY: VARIANT
<222> LOCATION: (6)...(6)
<223> OTHER INFORMATION: Xaa can be from 1 to 10 amino acids long
<220> FEATURE:
<221> NAME/KEY: VARIANT
<222> LOCATION: 6
<223> OTHER INFORMATION: Xaa = Any Amino Acid

<400> SEQUENCE: 3

Arg Gly Asp Asn Asp Xaa Ser Gly Asp Gly
1               5                  10

<210> SEQ ID NO 4
<211> LENGTH: 13
<212> TYPE: PRT
<213> ORGANISM: H. sapiens
<220> FEATURE:
<221> NAME/KEY: VARIANT
<222> LOCATION: 6, 7
<223> OTHER INFORMATION: Xaa = Any Amino Acid

<400> SEQUENCE: 4

Arg Gly Asp Asn Asp Xaa Xaa Pro Phe Ser Gly Asp Gly
1               5                  10

<210> SEQ ID NO 5
<211> LENGTH: 13
<212> TYPE: PRT
<213> ORGANISM: H. sapiens

<400> SEQUENCE: 5

Arg Gly Asp Asn Asp Ile Ser Pro Phe Ser Gly Asp Gly
1               5                  10

<210> SEQ ID NO 6
<211> LENGTH: 13
<212> TYPE: PRT
<213> ORGANISM: H. sapiens

<400> SEQUENCE: 6

Arg Gly Asp Asn Asp Met Ser Pro Phe Ser Gly Asp Gly
1               5                  10

<210> SEQ ID NO 7
<211> LENGTH: 13
<212> TYPE: PRT
<213> ORGANISM: H. sapiens

<400> SEQUENCE: 7
```

```
Arg Gly Asp Asn Asp Val Pro Pro Phe Ser Gly Asp Gly
1               5                   10

<210> SEQ ID NO 8
<211> LENGTH: 23
<212> TYPE: PRT
<213> ORGANISM: H. sapiens

<400> SEQUENCE: 8

Thr Asp Leu Gln Glu Arg Gly Asp Asn Asp Ile Ser Pro Phe Ser Gly
1               5                   10                  15

Asp Gly Gln Pro Phe Lys Asp
            20
```

METHOD FOR PROMOTING HARD TISSUE FORMATION

CROSS-REFERENCE

This application claims the benefit of U.S. Provisional Application Nos. 60/805,201 filed Jun. 19, 2006, 60/803,327 filed May 26, 2006, 60/747,255 filed May 15, 2006, 60/747,143 filed May 12, 2006 and 60/700,518 filed Jul. 18, 2005 all of which applications are incorporated herein by reference in their entirety noting the present application controls in the event of any conflict which an earlier application.

FIELD OF THE INVENTION

The present invention relates generally to formulations and methods for treating hard tissue by administering a combination of two or more peptides.

BACKGROUND OF THE INVENTION

It is well-documented that disorders of bone tissues causes numerous significant health problems on a world-wide basis. Because of such significant health problems with bone diseases, numerous efforts have been made to develop new therapeutic agents for bone disorders.

For example, several growth and/or differentiation factors are known to effect bone, cartilage, and dental tissues. Many of these have been evaluated for their ability to speed or alter the healing of defects in these tissues. Such factors include the molecules belonging to the transforming growth factor (TGF) and bone morphogenetic protein (BMP) family as well the epidermal growth factor (EGF), epithelial cell growth factor (ECGF), fibroblast growth factor (FGF), platelet derived growth factor (PDGF), insulin-like growth factor (IGF), and insulin-like growth factor binding protein (IGFBP) families.

Although many of these factors are known to promote proliferation, differentiation, maturation, or mineralization of osteoblastic cells, attempts to develop these factors as novel therapeutics have been limited by their lack of tissue specificity. Administration of these factors affect tissues other than skeletal tissues, which can result in undesirable activities.

For example, the administering of rhBMP-2 to soft tissue (e.g. subcutaneous injection) causes rapid formation of new bone in soft tissue. As a result of this response, use of rhBMP-2 has been limited and needs to be carefully applied in order to prevent calcification in undesirable locations.

A further limitation of using the above growth and/or differentiation factors as a therapeutic is the cost of manufacturing. The factors are all proteins manufactured by recombinant DNA methods, which require large-scale fermentation or cell culture processes. In addition, these manufacturing methods require highly specialized facilities, which further increase the cost of manufacturing. As a result, the manufacturing cost gets translated into a very expensive cost of treatment for using these products.

For example, a locally implantable collagen sponge that contains a BMP family molecule has been used as a medical device for spinal fusion therapies. However, the cost for such a procedure has provided a limitation of its availability to patients who could benefit from this type of treatment.

Accordingly, there is continued interest in the development of new therapeutics that would significantly reduce the cost of treatment. Of particular interest would be a novel therapeutic that would reduce the required dose of the already existing therapeutics.

Furthermore, growth factors other than those in the BMP family, such as those in the TGF, PDGF, EGF, FGF, and IGF families, should be explored as potential therapeutics. The utilization of other growth factors that reduce the efficacious dose and cost of therapies for existing growth factors therapeutics would be of great value to the orthopedic and related medical community and the patients that they serve.

SUMMARY OF THE INVENTION

The present invention relates to the formation or regeneration of new hard tissues such as bones, cartilage, and/or dental tissues. The invention comprises administering a first peptide which enhances the activity of a second peptide. More specifically, the first peptide enhances the biological activities and/or therapeutic effects of a second peptide which may be a hard tissue growth factor and/or differentiation factor. The first peptide and the second peptide may be together within a single formulation. Alternatively, the first and second peptides may be administered at substantially the same time or sequentially in either order. The first and second peptides may be present in the formulation or administered in substantially the same amount or different ratios relative to each other.

The first peptide comprises 10 to 50 amino acids having the amino acid sequence RGDBDXnSGZG, and wherein B, X, and Z are chosen from any amino acid residue and n is an integer between 1 and 10 (SEQ ID NO:3). The first peptide (e.g. a peptide of SEQ ID NO:8) is administered in an amount so as to enhance a characteristic of a second peptide chosen from differentiation, proliferation, maturation and mineralization of cells involved in the formation of hard tissue.

The second peptide (e.g., rhBMP-2) may be a growth factor which belongs to the family of transforming growth factor-beta (TGF-β). The TGF-β may belong to a family of bone morphogenic proteins (BMP).

Specific examples of the first peptide and the second peptide are provided here. The two peptides may be administered in a single formulation and the formulation may include the first and second peptides in equal amounts or different ratios. More specifically, formulations of the invention may be comprised of a pharmaceutically acceptable carrier (e.g. an absorbable collagen sponge (ACS)) and two proteins wherein the first protein is a protein chosen from

```
RGDBD(X)nSGZG                               (SEQ ID NO.1)
[B, X, and Z can be any amino acid,
n = 1~10]]

RGDND(X)nSGZG
[X and Z can be any amino acid, n =         (SEQ ID NO.2)
1~10]

RGDND(X)nSGDG
[X can be any amino acid, n = 1~10]         (SEQ ID NO.3)

RGDNDJJPFSGDG                               (SEQ ID NO:4)
[J can be any amino acid]

RGDNDISPFSGDG                               (SEQ ID NO.5)

RGDNDMSPFSGDG                               (SEQ ID NO.6)

RGDNDVPPFSGDG                               (SEQ ID NO.7)

TDLQERGDNDISPFSGDGQPFKD                     (SEQ ID NO.8)
``` and the second protein is chosen from molecules belonging to the transforming growth factor (TGF) and bone morphogenetic protein (BMP) family (e.g. rhBMP-2) as well the epidermal growth factor (EGF), epithelial cell growth factor (ECGF), fibroblast growth factor (FGF), platelet derived growth factor (PDGF), insulin-like growth factor (IGF), and insulin-like growth factor binding protein (IGFBP) families.

An aspect of the invention is that peptides such as rhBMP-2 are quite expensive and by combining such a peptide with a first peptide of the invention (e.g. a peptide of SEQ ID NO:8) it is possible to reduce the amount of the rhBMP-2 which is administered while obtaining substantially the same the desired therapeutic results as compared to administering a larger amount of rhBMP-2 without the first peptide. The second peptide may be the commercial available recombinant human bone morphogenic protein-2 (rhBMP-2) which may be on a commercially available type I bovine absorbable collagen sponge (ACS) sold as Helistat® by Integra Life Sciences, Plainsboro, N.J. The first peptide of the formulation which may be a peptide of SEQ ID NO:8 can be manufactured inexpensively in relatively large amounts. Thus, although the first and second peptides could be administered in equal amounts or different amounts there are economic reasons for administering the first peptide of the formulation in a relatively large amount relative to the second peptide. Peptides such as rhBMP-2 are very expensive to produce relative to the cost of producing a peptide of SEQ ID NO:8 Accordingly, if the first peptide is a peptide such as that of SEQ ID NO:8 and the second peptide is a peptide such as a bone morphogenic protein (rhBMP-2) the ratio of the second peptide to the first peptide may be any ratio which obtains an improved result compared to the same amount of only one of the peptides being used. However, because the second peptide such as rhBMP-2 is substantially more expensive as compared to the peptide of SEQ ID NO:8 there are economic reasons for using the two peptides in a formulation such that the first peptide such as the peptide of SEQ ID NO:8 is present in a larger amount relative to the second peptide such as rhBMP-2. Assuming the first number in the ratio represents the first peptide such as peptide of SEQ ID NO:8 and the second number represents an amount of the second peptide such as rhBMP-2, the formulation may be created where the ratio of the first peptide to the second peptide is 1:1 or more and that ratio can be extended up to 1:5,000 and possibly more. Ratios in intermediate amounts can also be used such as 1:2 through 1:5,000. Other ratios such as 1:5, 1:10, 1:50, 1:200, 1:300, 1:500, could be used and those skilled in the art could readily determine within a particular situation and formulation the desired ratio in terms of obtaining the most therapeutic effect at the most economic cost. The ratios of one protein or peptide to another are ratios based on the weight of the protein or peptide used in the formulation.

A specific example of the invention is a formulation which is specifically designed for promoting hard tissue formation and regeneration. The formulation may be comprised of a pharmaceutically acceptable carrier such as an injectable carrier having therein the first protein and the second protein of the invention. Still more specifically, the formulation may be comprised of a pharmaceutically acceptable carrier which may by an ACS or an injectable carrier a first protein having the SEQ ID NO:8 and the second protein in the form of rhBMP-2. The first and second proteins may be present in equal amounts or in any different ratios including those indicated above. Further, although specific formulations described here include a single first protein and a single second protein it is understood that multiple proteins from each group may be included within a formulation or may be administered separately, at the same time or sequentially at different times.

An aspect of the invention is that by including the first peptide of the invention it is possible to administer the second peptide in an amount which would be below levels which would (by itself) be expected to provide a therapeutic result. Thus, a formulation can be prepared by combining a pharmaceutically acceptable injectable carrier with a peptide of SEQ ID NO:8 and rhBMP-2 wherein the amount of rhBMP-2 is an amount which would not be therapeutically effective in the absence of the peptide of SEQ ID NO:8.

A method to promote biological processes to form or regenerate new hard tissues such as bones, cartilage, and/or dental tissues is disclosed wherein the method may be carried out at substantially reduced costs as compared to the use of rhBMP-2 alone. More specifically, the present invention is a method of enhancing the biological activities of a hard tissue growth and differentiation factor characterized by specific and selective upregulation and/or extension of the retention time of the intracellular enzymes and signaling molecules that play important roles to proliferate, differentiate, maturate, and/or mineralize hard tissue forming cells. This invention provides the medical community with a method of treating hard tissue disorders and of improving the efficacy of currently used practices. This method is also expected to result in a significantly reduced cost to patients. By administering the first protein which may be a protein such as that of SEQ ID NO:8 it is possible to reduce the amount of the second protein such as rhBMP-2 and still obtain the desired therapeutic effect that would be obtained when administering optimal concentrations of rhBMP-2.

Another aspect of the invention is a kit for administration to the patient. The kit may comprise instructions with respect to how to combine and administer the components. The components may include a pharmaceutically acceptable carrier. The carrier may be an injectable carrier or it may be an implantable absorbable material such as an implantable absorbable sponge including the type I bovine absorbable collagen sponge (ACS). Further, the kit may include a pre-measured and packaged amount of a first peptide which may be any first peptide of the type described herein including a first peptide of SEQ ID NO:8. The kit may further include a second peptide which may be any second peptide of the type described herein which may include rhBMP-2. The kit may include multiple different versions of the first peptide. Further, the kit may include multiple different versions of the second peptide. In one version the kit includes separately packaged components of the carrier in the form of the absorbable collagen sponge, a first peptide of SEQ ID NO:8 and a second peptide which is rhBMP-2 wherein the peptide of SEQ ID NO:8 and rhBMP-2 are present in measured amounts in a ratio capable of obtaining a desired therapeutic effect in an economically advantageous manner.

These and other objects, advantages, and features of the invention will become apparent to those persons skilled in the art upon reading the details of the inventions as more fully described below.

BRIEF DESCRIPTION OF THE DRAWINGS

In accordance with the present invention, the invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

DETAILED DESCRIPTION OF THE INVENTION

Figure 1:
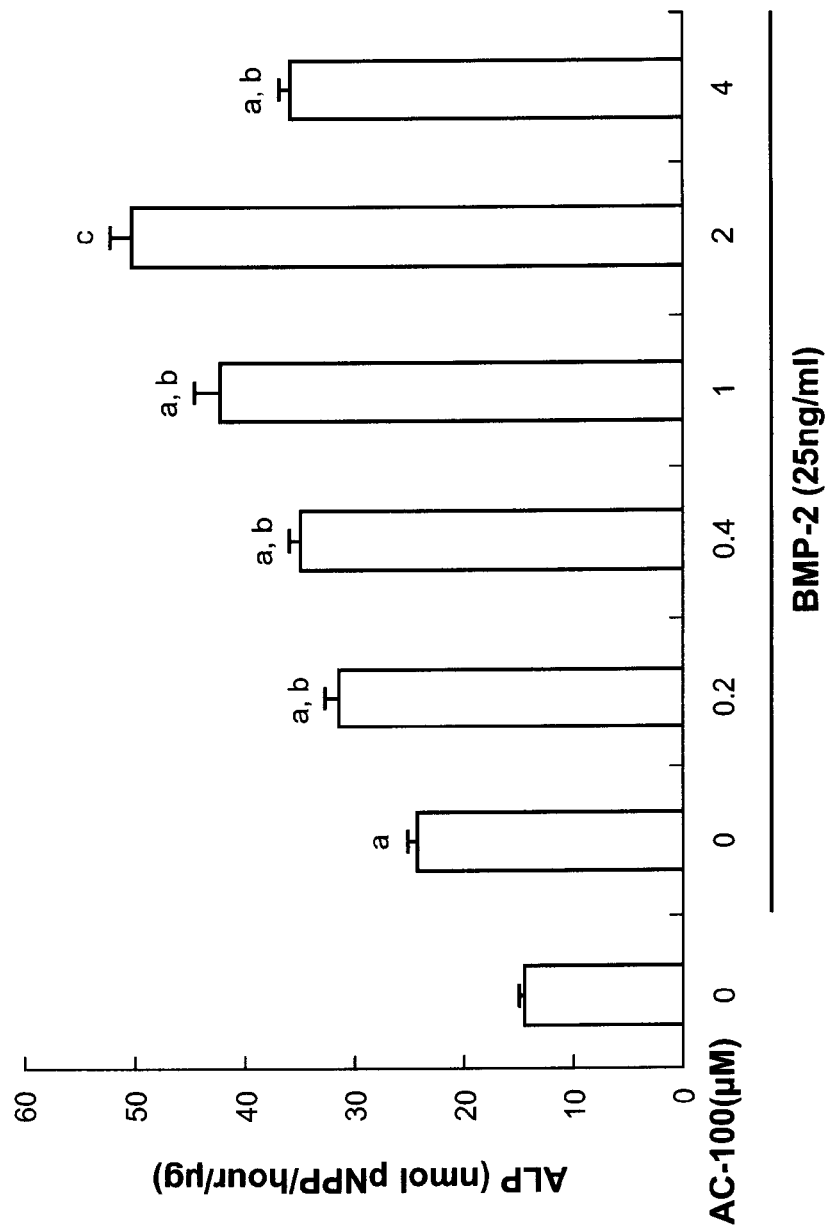
FIG. 1 is a bar graph showing the dose dependent upregulation of alkaline phosphatase (ALP) activity in mouse primary osteoblasts cultured with a suboptimal concentration of rhBMP-2 when a different concentration of the peptide of SEQ ID No. 8 were added to the cultures.

Before the present methods and formulations of the invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a protein" includes a plurality of such proteins and reference to "the peptide" includes reference to one or more peptides and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "treatment", "treating" and the like are used here to describe obtaining a desired pharmacological and/or physiological effect which effect is an effect on hard tissue formation, regeneration, growth and the like. The effects may be prophylactic in terms of completely or partially preventing hard tissue loss and/or may be therapeutic in terms of partially or completely curing an adverse condition which is attributed to hard tissue loss. Accordingly, "treatment" as used here is intended to cover treating a mammal and in particular a human to include:

(a) preventing a disease or condition from proceeding in manner which prevents further loss of hard tissue or further acceleration loss of hard tissue;

(b) inhibiting a disease or condition, i.e. arresting a condition which leads to hard tissue loss; and/or (c) relieving a disease or condition thereby causing regression of the disease or condition and thereby promoting hard tissue formation, regeneration and/or growth. By carrying out the invention it is possible to enhance differentiation, proliferation, maturation and/or mineralization of cells involved in the formation of hard tissue.

The terms "synergistic", "synergistic effect" and the like are used herein to describe improved treatment effects obtained by combining the administration of one or more proteins. Although a synergistic effect in some fields is meant an effect which is more than additive (e.g. 1+1=3), in many fields relating to bone disease an additive (1+1=2) or even less than additive (1+1=1.6) effect can be interpreted as synergistic. For example, one cannot treat any bone disease merely by adding together two known pharmaceuticals each of which are 50% effective in treatment to obtain a 100% effective treatment. Thus, in some situations adding two components together can actually have a negative effect and obtain results which are less desirable than when either drug is used by itself. Further, as used herein synergistic means that one of the components (e.g. rhBMP-2) may be used in a lesser amount when combined with a second component (e.g. SEQ ID NO:8) and still obtain the same desired effect as if the rhBMP-2 component where present in a larger amount. Thus, in connection with the invention by combining the first protein such as that of SEQ ID NO.:8 with the second protein such as rhBMP-2 the amount of rhBMP-2 needed to obtain desired therapeutic results can be reduced. That reduction may be 10%, 20%, 50%, 75% or more as compared with the dosing needed to obtain the desired result without the administration of the first protein. A synergistic effect is also obtained with respect to the economic value of formulations of the invention. Thus, when very large amounts of the first protein such as a protein of SEQ ID NO:8 are used very small amounts of the second protein such as rhBMP-2 are used. Because the rhBMP-2 is substantially more expensive to manufacture as compared to a protein of SEQ ID NO:8 synergistic economic results are obtained even when substantially the same therapeutic results are obtained. Thus, when large amounts of the first protein such as a protein of SEQ ID NO:8 are used the amount of the second protein may be one half or less, one tenth or less or even one hundredth or less of the dosing that might be required to obtain a desired therapeutic effect in the absence of the first protein of SEQ ID NO:8.

The terms "simultaneous" and "sequential" in terms of administering formulations of the invention are used herein to mean that the first peptide and the second peptide may be administered at exactly the same time or one after another with consideration to normal medical procedures and results being obtained. Thus, simultaneous may mean that the two compounds are present within a single formulation or that they are administered at the same point of treatment. "Sequentially" may mean that they are administered sequentially one after another from the same syringe or from different syringes. What is important is that the first and second peptides be administered in such a manner that the first peptide and the second peptide can have an opportunity to physiologically interact in terms of the desired treatment being sought.

INVENTION IN GENERAL

Formulations of the invention are administered for enhancing hard tissue formation. The formulations may be administered by implanting them after putting drug on an absorbable collagen sponge as a carrier or administered by injection with the proteins in a pharmaceutically injectable carrier. The formulation may include one, two or more proteins. In one embodiment the formulation administered to a human patient includes a first protein which is a protein which is encompassed by the general sequence of SEQ ID NO: 1, in combination with the second protein which is chosen from molecules belonging to the transforming growth factor (TGF) and bone morphogenetic protein (BMP) family (which includes rhBMP-2), as well the epidermal growth factor (EGF), epithelial cell growth factor (ECGF), fibroblast growth factor (FGF), platelet derived growth factor (PDGF), insulin-like growth factor (IGF), and insulin-like growth factor binding protein (IGFBP) families.

Formulations of the invention used in treating a mammal may include the carrier and only one protein (e.g. SEQ ID NO:8) and may be present in a kit wherein a second protein (e.g. rhBMP-2) is also present in a pre-measured amount and packaged with a pharmaceutically acceptable carrier which may be an absorbable collagen sponge (ACS) or an injectable carrier. The two proteins may be packaged together for simultaneous or sequential administration. Formulations or kits of the invention may be designed in a way so as to obtain a desired therapeutic result while minimizing the amount of the second protein present in the kit or formulation. Because the first protein such as the protein of SEQ ID NO:8 is relatively inexpensive to produce and the second protein (e.g. rhBMP-2) is quite expensive those skilled in the art will recognize that formulating to include large amounts of the first protein and small amounts of the second protein can provide desired therapeutic results in a manner which is highly economical.

The second peptide used in treating a mammal may be the commercial available recombinant human bone morphogenic protein-2 (rhBMP-2) which may be on a commercially available type I bovine absorbable collagen sponge (ACS) sold as Helistat® by Integra Life Sciences, Plainsboro, N.J.

The method of the invention enhances the activities of growth and/or differentiation factors, that are known to promote one or more of proliferation, differentiation, maturation, and mineralization of the cells in the hard tissue forming cell lineage including but not limited to osteoblasts, odontoblasts, ameloblasts, and cementoblasts, and thereby promote new hard tissue formation.

In a particular embodiment of this invention, the method of this invention specifically enhances the activities of differentiation factors that usually promote one or more of differentiation, maturation, and/or mineralization of the hard tissue forming cells.

The method is characterized by using a peptide containing amino acid sequence that is generally defined by the SEQ ID No. 1. It was discovered that, by adding the peptide to an in vitro or in vivo skeletal tissue forming system, the hard tissue formation that was promoted by hard tissue growth and/or differentiation factors was significantly enhanced and that the necessary amount of such factors was significantly reduced. Further, this significant synergistic effect between the hard tissue growth and/or differentiation factors and the peptides containing SEQ ID No. 1 is highly selective to the hard tissues. In other words, this unique enhancing effect by the peptides containing SEQ ID No. 1 is expected only in a tissue that has committed to become a hard tissue.

This unexpected and significant finding provides the medical community with an improved method to heal a hard tissue defects. The use of such peptides minimizes the necessary amount of such growth and/or differentiation factor required to exert maximum activity, thereby reducing the overall cost of treatment significantly.

Any of the peptides containing SEQ ID No. 1 can be manufactured by widely used chemical synthesis methodology of the peptides and the cost of goods thereof can be significantly lower than recombinant growth and/or differentiation factors.

In addition, because the biological activities of the peptides containing SEQ ID No. 1 are expressed only in a hard tissue environment, the administration route of the peptides to the subjects in need is not limited even if the other growth and/or differentiation factors may have certain limitation in their method of administration. In other words, the peptides containing SEQ ID No. 1 can be formulated and administered in variety of manners depending upon the therapeutic procedure.

Another characteristic feature of this invention is that by adding the peptides containing SEQ ID No. 1, the expression and activities of cyclooxygenase-2 (COX-2) in the hard tissue forming cells such as osteoblasts, odontoblasts, cementoblasts, and ameloblasts, are significantly upregulated. This significant upregulation of COX-2 is observed in a dose dependent manner following addition of the peptide containing SEQ ID No. 1.

Furthermore, the production of prostaglandin E2 (PGE2) by such hard tissue formation cells is significantly upregulated by the method.

It has been known that PGE2 promotes the proliferation of hard tissue formation cells. Therefore, the local upregulation of PGE2 in hard tissue formation cells is desirable.

Nagel, et. al. demonstrated that the peptide of SEQ ID No. 8, which is also called AC-100 and under Phase II clinical developments for multiple hard tissue treatments, upregulated COX-2 in human mesenchymal stem cells (Journal of Cellular Biochemistry, 2004).

Also, Middleton-Hardie, et. al. has shown that the peptide of SEQ ID No. 8 dose dependently upregulated the production of PGE2 in mouse calvaria organ culture assay (27th Annual Meeting of the American Society for Bone and Mineral Research 2005, in press). It has been also shown that some hard tissue growth factors such as BMP increased the production of PGE2 by osteoblastic cells.

However, when the peptides containing the SEQ ID No. 1 are used with a suboptimal concentration of rhBMP-2, which marginally upregulated COX-2 or PGE2 alone, either COX-2 or PGE2 were significantly upregulated in a dose dependent manner of the peptides following the addition of the peptides containing SEQ ID No.1.

For example, addition of the peptide of SEQ ID No. 8 alone to human mesenchymal cells in culture did not result in a significant increase in PGE2. Since enhancement of PGE2 occurs in organ cultures and when rhBMP-2 is present (even at suboptimal concentrations), it is believed that the peptide of SEQ ID No. 8 acted by substantially enhancing the differentiation activities of rhBMP-2 (whether added exogenously or produced locally in bone or by bone cells).

Smad molecules (1~8) are known to play important roles in intracellular signaling of members of the TGF-β and BMP families. In hard tissue forming cells, Smads 1, 5, and 8 are known to be activated by differentiation factors such as BMP family molecules. Such activation of Smad molecules can be observed via a phosphorylation event that occurs within 10-20 minutes after stimulation. Typically, the retention time of such phosphorylated Smad molecules is short lived, usually disappearing within about 0.5 to 12 hours after the initial stimulation of the cells.

Bone forming cells, such as the MC3T3 cells are stimulated with both rhBMP-2 and a peptide containing SEQ ID No. 1, intracellular Smad molecules (in particular Smads 1, 5, and 8) are phosphorylated and remain phosphorylated for up to 48 hours. This strongly suggests that peptides containing SEQ ID No. 1 have the ability to extend the activity of hard tissue forming cells and thereby enhance the hard tissue formation.

This correlation between the enhancement of hard tissue formation and extension of the retention time of the phosphorylated Smad molecules is extremely useful to design or identify a novel molecule that can enhance hard tissue formation. Those skilled in the art can establish an assay system to observe the retention time of the phosphorylated Smad molecules in a hard tissue forming cell and use it to screen a new chemical entity that stimulates hard tissue formation.

Any compound that can extend the retention time of the phosphorylated Smad molecule in hard tissue forming cells and a method to identify such a compound using the screening system to evaluate the retention time of the phosphorylated Smad molecule in hard tissue forming cells are within the scope of this invention.

It has been known that BMP causes bone formation when administered or implanted in mammals when given. The activity can be enhanced when given in the appropriate delivery vehicle. As indicated in Example 6, new bone tissue was locally formed in about 20 days after a polymer comprising polylactic acid (PLA), polyethylene glycol (PGE), and a linker (DX) containing 5 µg or higher amount of rhBMP-2 was implanted to mouse dorsal muscle. With lower, suboptimal doses of rhBMP-2, the there is minimal or no bone formation. Specifically in this case when a 3 µg dose was used, there was substantially less bone formation compared to administration of a 5 µg dose.

Figure 3:
FIG. 3 is an image of a gel which demonstrates the expression of phosphorylated Smads 1, 5, and 8 (as a total) indicated by Westein blot from MC3T3 cells at different time points. Cells were cultured with a suboptimal concentration of rhBMP-2 either with or without the peptide of SEQ ID No. 8.

Varying amounts of peptide of SEQ ID No. 8 were added to the same polymer containing as suboptimal dose, 3 µg of rhBMP-2. However, as indicated in FIG. 3, when a peptide of SEQ ID No. 8 dose was added to the suboptimal dose of rhBMP-2, there was a significant and dose dependent increase in bone formation. When given at 50 µg/mL or higher, the degree of new bone formation was similar or superior to the amount of bone formed using an optimal dose of rhBMP-2.

Equivalent or comparable results are obtained in the same experiments when different peptides that have the amino acid sequence defined by SEQ ID No. 1 are used.

These in vivo results clearly suggest that a peptide containing SEQ ID No.1 can significantly reduce the required amount of rhBMP-2 when it is used with such peptide to form a new bone in the mammals. This significant reduction of the required amount of rhBMP-2 is extremely beneficial to the medical practice due to a lower cost and a lower risk of ectopic calcification form higher doses of rhBMP-2.

Since hard tissue forming cells are in the same lineage, a similar synergistic effect is expected in dental hard tissues such as dentin, enamel, and cementum, which are formed by odontoblasts, ameroblasts, and cementum, respectively.

The co-use of the peptides containing SEQ ID No. 1 for above hard tissue formation purposes is not limited to use with BMP family molecules. A similar effect can be expected when the peptides are used with other hard tissue growth or differentiation factors including but no limited to the molecules belonging to the families of TGF (BMP family is a part of it), EGF, PDGF, FGF, IGF, and IGFBPs.

The peptides used herein are defined by their containing of specific amino acid sequences specified by SEQ ID No. 1. The peptides can be in the sizes of approximately 10 to 50 amino acids as far as they contain the amino acid sequence specified by SEQ ID No. 1. The peptides used in this invention are not necessarily linear peptides but can be cyclic or branched peptides. A peptide longer than 50 amino acids that contains a tandem sequence of the sequence units of this invention is also within the scope of this invention. Multimers of the peptides containing SEQ ID No. 1 are also within the scope. Such multimers can be dimers, trimers, tetramers, pentamers, hexamers, heptamers, octamers, nonamers, decamers, etc.

The minimum size of the peptide of this invention has an amino acid sequence of RGDBDXSGZG wherein B, X, and Z can be any amino acid. The peptides containing the general amino acid sequence of SEQ ID No. 4 demonstrate higher biological activities than other sequences for the purpose of this invention whereas SEQ ID No. 8 exhibits the highest activities.

The SEQ ID No. 5 and 8 are equivalent to the amino acid number 247-259 and 242-264, respectively, of a known human protein named matrix extracellular phosphocglycoprotein (MEPE). The SEQ ID No. 6 is a macaque monkey orthologue of the human sequence of SEQ ID No. 5. The SEQ ID No. 7 is rodent (common between mouse and rat) orthologue of the same portion. All of these orthologues of MEPE contain sequences within the scope of the SEQ ID No. 1 that promote proliferation, differentiation, maturation, and mineralization of hard tissue forming cells in an equivalent manner.

In summary, a method to promote or enhance new hard tissue formation was presented in that a peptide comprising about 10 to 50 amino acid that contains amino acid sequence specified by SEQ ID No. 1. This peptide reduced the quantity of a bone differentiation and/or formation factor (e.g. rhBMP-2) needed to promote effective new bone formation. Further investigation suggests that this may be occurring by a mechanism involving extension of the life time of specifically phosphorylated Smad molecules known to be involved in the molecular signaling pathway responsible for bone formation.

KITS

One kit in accordance with the invention includes one or more absorbable collagen sponges of the type generally used commercially in connection with rhBMP-2. The sponges are present with a solution of the first protein such as a peptide of SEQ ID NO:8 and a separate container comprising the second protein such as rhBMP-2. In another version of the kit the first protein such as the peptide of SEQ ID NO:8 and the second protein such as rhBMP-2 are present in the same solution container. Including the two proteins in different containers is advantageous in that if the shelf life of the two containers is different it may not be necessary to discard both containers when the shelf life of only one has expired. Further, the kits can be designed so that the absorbable collagen sponge or sponges are of the appropriate size to absorb the amount of solution from one or both of the containers containing the first and second peptides. Still further, the first and second peptides will be included in separate containers or mixed in a single container in desired ratios such as the ratios provided above. As previously indicated these ratios generally provide for relatively large amounts of the first protein such as the peptide of SEQ ID NO:8 and relatively small amounts of the second protein such as rhBMP-2.

BONE MORPHOGENIC PROTEIN

The second protein used in formulations of the present invention can be a naturally occurring protein or a recombinantly produced version of such a naturally occurring protein. An example of such a protein is bone morphogenic protein-2 (BMP-2) which in its recombinant version is referred to as recombinant human bone morphogenic protein-2 (rhBMP-2). Information relating to bone morphogenic protein is contained within the following publications which are incorporated herein by reference. BioDrugs. 2002; 16(5): 376-7. Journal of Orthopaedics 2005;2(4)e3; U.S. Pat. Nos. 5,108, 922; 5,187,07; 5,318,898; 5,459,047; 5,618,924; 5,631,142.

Bone morphogenic protein along with a first protein of the invention may be combined with a suitable pharmaceutically acceptable carrier such as the type I bovine absorbable collagen sponge (ACS).

A therapeutic formulation of the present invention is applied to the sites of bone and/or cartilage damage (e.g., bone fractures, osteotomies, etc.), thus providing localized delivery of the therapeutic protein composition of the invention. For example, a therapeutic protein composition can be applied either by injection in a suitable carrier (e.g., an oily solvent such as arachis oil or an injectible bone cements) to the site of interest or, in cases of open surgery, by local application thereto of such compounds in a suitable carrier such as bone-wax, demineralized bone powder, polymeric bone cements, bone sealants, etc. Alternatively, local application can be achieved by applying a solution or dispersion of the therapeutic protein composition in a suitable carrier onto the surface of, or incorporating it into solid or semi-solid implants conventionally used in orthopedic surgery, such as prostheses, dacron-mesh, Gore-tex™, gel-foam and kiel bone, and/or a collagen sponge/matrix. For example, absorbable collagen sponges reconstituted from bovine tendon and collagen based matrices derived from demineralized/guanidine-extracted bovine bone are two delivery materials currently being used for delivery of BMP to sites of interest (see e.g., Infuse™, Medtronic, Inc.; InductOs™, Wyeth/Astellas BV).

In certain embodiments, a therapeutic formulation of the invention includes a matrix capable of delivering a therapeutic protein composition such as SEQ ID NO:8 with rhBMP-2 to the site of bone and/or cartilage damage while providing a structure for the developing bone and cartilage. Such matrices may be formed of any convenient material including those materials presently in use for other implanted medical applications. Such formulations may desirably be applied to a sponge which is implanted, encapsulated or injected in a viscous form for delivery to the site of bone, cartilage or tissue damage. The choice of matrix material can be based on several factors, including biocompatibility, biodegradability, mechanical properties, cosmetic appearance and interface properties. The particular application of a specific therapeutic formulation will impact its design and implementation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability.

The dosage regimen for therapeutic formulations of the present invention such as SEQ ID NO:8 with rhBMP-2 will be determined by a number of factors which can affect the action of the therapeutic protein composition of a formulation of the invention, including amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of vehicle, carrier, or matrix employed as well as the identity of the therapeutic protein or proteins in the formulation. Efficacy of treatment can be monitored in the clinic by periodic assessment of bone growth and/or repair, e.g. using x-rays.

In certain embodiments, the total dose in weight of the therapeutic protein composition of a formulation of the invention such as SEQ ID NO:8 with rhBMP-2 can be from microgram (fig) to milligram (mg) quantities (e.g., from 1 μg to 100 mg, including from 2 μg to 50 mg, such as from 10 μg to 25 mg, 100 μg to 10 mg, etc.). As indicated above, the total dose can be determined by a number of factors. In certain embodiments, the therapeutic protein composition will be present in the formulation at a concentration (i.e., dosage in weight of therapeutic protein composition/weight of total formulation) that ranges from 0.1 mg/ml to 5 mg/ml, including 0.5 mg/ml to 4 mg/ml, such as 1 mg/ml to 3 mg/ml, e.g., 2 mg/ml.

Therapeutic protein compositions in formulations of the invention may contain two or more proteins. In one embodiment the formulation includes a first protein which is a protein which is encompassed by the general sequence of SEQ ID NO: 1, in combination with the second protein which is chosen from molecules belonging to the transforming growth factor (TGF) and bone morphogenetic protein (BMP) family as well the epidermal growth factor (EGF), epithelial cell growth factor (ECGF), fibroblast growth factor (FGF), platelet derived growth factor (PDGF), insulin-like growth factor (IGF), and insulin-like growth factor binding protein (IGFBP) families. In certain of these embodiments, the ratio of the second protein to the first protein in therapeutic formulations of the invention range from 1:1 or more to 1:5,000 or more, including from 1:1 or more to 1:1,000 or more, such as from 1:2 or more to 1:500 or more.

Those skilled in the art will recognize that substantial additional information relating to BMP which is also referred to herein as BMP-2 and rhBMP-2 can be found within the literature including numerous issued U.S. Patents. Further, specific formulations including other proteins which promote hard tissue formation growth can be found in the literature in connection with the present invention a first protein which is encompassed by SEQ ID NO: 1 is combined with any of these proteins which promote hard tissue formation and growth in order to enhance the therapeutic effect while using the smaller amounts of the protein.

MANUFACTURE FOR A METHOD

The formulation and/or kit may be manufactured for carrying out a method comprising:
  administering to a patient a first peptide comprising 10 to 50 amino acid residues having an amino acid sequence of RGDBD(X)nSGZG (SEQ ID NO: 1), wherein B, X, and Z can be any amino acid residue and n is any integer between 1 and 10; and
  further administering to the patient a second protein chosen from the group comprising a transforming growth factor (TGF), a bone morphogenetic protein (BMP), epidermal growth factor (EGF), epithelial cell growth factor (ECGF), fibroblast growth factor (FGF), platelet derived growth factor (PDGF), insulin-like growth factor (IGF), and an insulin-like growth factor binding protein (IGFBP).

In the method the patient may be a human and the method may be carried out in order to enhance hard tissue formation activity. The method may be carried out to extend retention time of a phosphorylated Smad molecule. The method may be carried out in order to reduce time required to dephosphoiylate Smad molecules. The method may be carried out in order to reduce time required to degrade phosphorylated Smad molecules in hard tissue forming cells.

The cells treated may be tissue forming cells chosen from the group of: (a) cells of a lineage of osteoblast wherein the hard tissue is in the form of bone tissue; (b) cells of a lineage of ameloblast wherein the hard tissue is in the form of enamel; (c) cells of a lineage of odontoblast wherein the hard tissue is in the form of dentin; and (d) cells of a lineage of cementoblast wherein the hard tissue is in the form of cementum.

The first peptide and the second peptide may be administered by injection. The first peptide may be a peptide of SEQ ID NO:8 and the second peptide is a recombinant human bone morphogenic protein-2 (rhBMP-2). The first protein and the second protein may be administered at the same time. The first protein and the second protein may be administered on an absorbable collagen sponge (ACS).

The formulation and/or kit may be manufactured for treating a disease characterized by a hard tissue defect comprising:
  (a) administering a peptide comprising about 10 to 50 amino acids containing an amino acid sequence of RGDBD (X)nSGZG (SEQ ID NO: 1), where B. X, and Z can be any amino acid residue and n is any integer between 1 and 10; and
  (b) administering a molecule that promotes growth of a hard tissue, and a carrier.

The method may be carried out wherein (a) and (b) are administered simultaneously. The method may be carried out wherein (a) and (b) are administered sequentially with the peptide being administered prior to the molecule that promotes growth of a hard tissue. The method may be carried out wherein (b) and (a) are administered sequentially with the molecule that promotes growth of hard tissue being administered prior to the peptide. The method may be carried out wherein administering (a) and (b) upregulates and/or activates cyclooxygenase-2 in the treated hard tissue. The method may be carried out wherein prostaglandin $E_2$ production is increased by the treated hard tissue. The method may be carried out wherein degradation time of phosphorylated Smad molecules is extended in treated hard tissue cells.

A kit and/or formulation is manufactured for carrying out a method of enhancing a hard tissue forming cell comprising extending the retention time of phosphorylated Smad 1, 5, and 8, wherein enhancing promotes proliferation, differentiation, maturation, or mineralization.

A kit and/or formulation is manufactured for carrying out a method of treating a disease characterized by a hard tissue defect comprising:
  administering one or more pharmaceutically active molecules that are capable of extending phosphorylated Smad molecules retention time in hard tissue forming cells.

A kit and/or formulation is manufactured for carrying out a method of regenerating cartilage comprising:
  administering to a patient a pharmaceutically active amount of a composition comprising polypeptides having the sequence of SEQ ID No. 1 as defined here.

A kit and/or formulation is manufactured for carrying out a method of treatment, comprising:
  administering to a patient a therapeutically effective amount of a formulation comprising a pharmaceutically acceptable carrier and a peptide chosen from a peptide of any of SEQ ID NO:1-SEQ ID NO:8 as defined herein.

The method may further comprise repeatedly administering the formulation to the patient periodically over a period of time in a manner so as to promote growth of hard tissue.

The method may further comprise administering a second drug which initials hard tissue formation.

The method may be carried out wherein the second drug is a recombinantly produced bone morphogenetic protein (BMP).

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

Increase of Alkaline Phosphatase (ALP) Activity in Primary Osteoblasts Under Suboptimal Concentration of BMP-2 with the Addition of the Peptide of SEQ ID No. 8 to the Culture Materials and Methods: Primary osteoblasts collected from fetal mouse calvaria were cultured under 0 or 25 ng/mL BMP-2. The peptide of SEQ ID No. 8 was added to this culture system at 0, 0.2, 0.4, 1.0, 2.0, and 4.0 µM. The levels of ALP were evaluated on days 0, 3, and 7.

Results: As shown in FIG. 1, ALP activity in osteoblastic cells was significantly increased in the groups treated with BMP-2 and the peptide of SEQ ID No. 8 in a dose dependent manner. In the 2 μM of the peptide of SEQ ID No. 8 treatment group, ALP activity was increased about 3 times as compared with that in the control group and 2 times as compared with that in the BMP-2 treated cells without addition of the peptide.

Discussion: These results demonstrated that the peptide of SEQ ID No. 8 significantly increased the ability of BMP-2 to positively influence the differentiation of pre-osteoblastic cells into osteoblasts.

Example 2

Increase in COX2 Levels in Primary hMSC with Addition of Different Doses of the Peptide of SEQ ID No. 8

Materials and Methods: The effect of the peptide of SEQ ID No. 8 treatment on gene expression was assessed in the Clonetics hMSC cells using gene expression microarray analysis as previously described (Locklin et al., 2001). Briefly, cells were plated in five T-150 vented flasks at a density of 1.0×106 cells per flask in growth medium and cultured at 37° C. for 48 hours. Flasks containing either vehicle alone or the peptide of SEQ ID No. 8 (1000 ng/ml) were cultured for 24 hr or for 48 h in standard differentiation medium. At each time point, the vehicle and treatment flasks were trypsinized, cells removed and total RNA was extracted for analysis via the Qiagen Rneasy Kit (Qiagen). 8 μg of total RNA were amplified and biotin labeled. The mixture was hybridized to a U95A human gene expression microarray (Affymetrix) containing probes for 12,600 human genes. The chips were then washed, stained with phycoerythrin-streptavidin and read with an Affymetrix scanner. Hybridization intensity values to mRNA frequency were calculated in molecules per million. Analysis of intensity values was conducted using Spotfire Decision Site (Somerville, Mass.) software.

Results: Only mRNAs that were changed by the treatment with the peptide of SEQ ID NO. 8 by 2-fold or more were considered. The only mRNA that was changed by this extent at both time intervals was COX-2: it was increased at 24 h by 3.6-fold and at 48 h by 2.2-fold.

Discussion: These data demonstrated that the peptide of SEQ ID No. 8 increased (by ~3-fold) the mRNA for cyclooxgenase-2 (COX-2), an inducible enzyme required for prostaglandin synthesis. Thus the peptide of SEQ ID NO. 8 has the potential to induce the synthesis of PGE2 which is known to have positive effects on bone formation.

Example 3

Potentiation of BMP-2 Stimulated $PGE_2$ Production by MC3T3 Cells by the Peptide of SEQ ID No.8

Methods: MC3T3-E1 subclone 4 cells are neonatal mouse derived calvarial preosteoblasts with fibroblast morphology. This subclone exhibits high levels of osteoblast differentiation when grown in the presence of ascorbic acid and inorganic phosphate. For this experiment the MC3T3 cells were plated 105 cells per well in 24 well plates in growth medium (alpha MEM+1 mM sodium pyruvate+10% fetal bovine serum (FBS)). After 24 hours of culture the media was removed and replaced with assay media (alphaMEM+1 mM sodium pyruvate+2% FBS) containing the test substances. Each test group utilized 4 wells. After incubation for a further 24 hours the media was removed and the levels of PGE2 were determined using an ELISA (R&D Systems).

Figure 2:
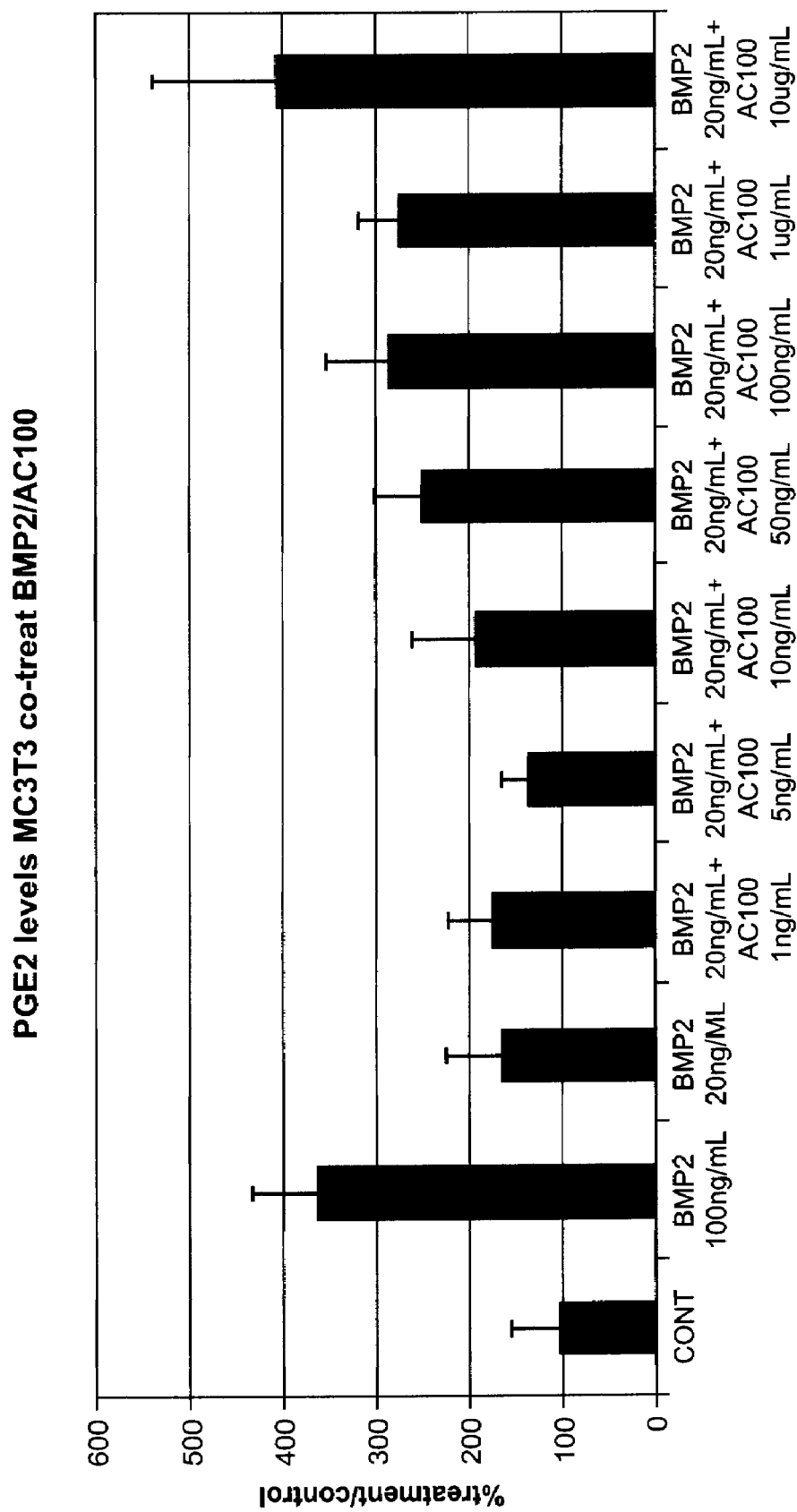
FIG. 2 is a bar graph showing a dose dependent production of prostaglandin E2 by MC3T3 cells cultured with a suboptimal concentration of rhBMP-2 plus varying doses of the peptide of SEQ ID No. 8 was added to the culture.

Results: The peptide of SEQ ID No. 8 increases the BMP-2 induced PGE2 production as exhibited by FIG. 2.

Example 4

Retention of BMP-Activated Phosphorylated Smad 1, 5, and 8 in Primary Mouse Osteoblasts When the Peptide of SEQ ID No. 8 Was Added to the Cell Culture Materials and Methods: Primary osteoblasts collected from fetal mouse calvaria were cultured with 0 or 25 ng/mL of BMP-2 with the addition of 0 or 2 μM of the peptide of SEQ ID No. 8 to the culture system. Phosphorylation of Smad1/5/8 was evaluated by Western blotting at 0, 0.5, 1, 2, 12, 24, 48 and 72 hours.

Results: Under these conditions BMP-2 induced phosphorylation of Smad1/5/8, which was detectable from 0.5 to 12 hrs. The addition of 2 μM of the peptide of SEQ ID No. 8 to BMP-2 induced a prolonged phosphorylation of Smad1/5/8 which was detectable from 0.5 to 48 hrs (FIG. 3).

Discussion: These data indicated that the ability of the peptide of SEQ ID NO. 8 to potentate the activity of BMP-2 may be due at least in part on the ability of the peptide to significantly prolong the half-life of the phosphorylated Smad1/5/8 proteins, which are integral part of the signal transduction pathway of BMP-2 and other bone anabolic agents.

Example 5

Increase in the Production of $PGE_2$ in Mouse Calvaria Organ Culture Assay with Suboptimal Concentration of BMP-2 with Addition of different Concentration of the Peptide of SEQ ID No. 8

Methods: Calvarial organ cultures have been used for many years to study the regulation of bone formation and bone resorption. An advantage of this method compared to in vivo studies is the absence of confounding effects (such as hormonal and mechanical influences) meaning a more direct effect of the test substances on bone tissue can be determined. Also compared to isolated cell systems, interrelationships between the different cell types in the bone and between these cells and the bone matrix are preserved.

Briefly, hemi-calvariae were isolated from 4 day old Swiss Webster mice and incubated in media on steel mesh grids. The peptide of SEQ ID NO. 8 (1, 10, 100 μg/mL) was added daily to the culture for seven days and a BMP-2 (40 ng/mL) control group was treated at days 1 and 4. Samples of the conditioned media were collected daily for analysis of PGE2 concentration (R&D Systems ELISA kit). At the end of the culture the bones were analyzed for new bone formation and number of osteoblasts using histology.

Figure 4:
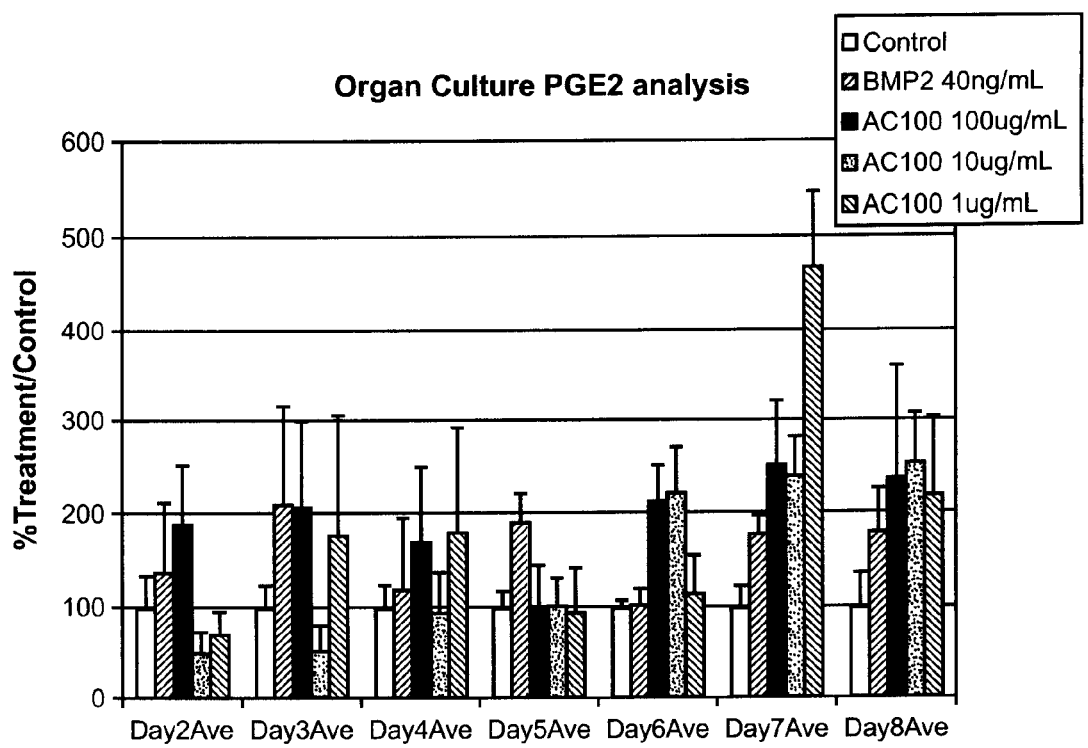
FIG. 4 is a bar graph which production of PGE2 by calvaria when it was isolated and cultured with different doses of the peptide of SEQ ID No. 8.
Figure 5:
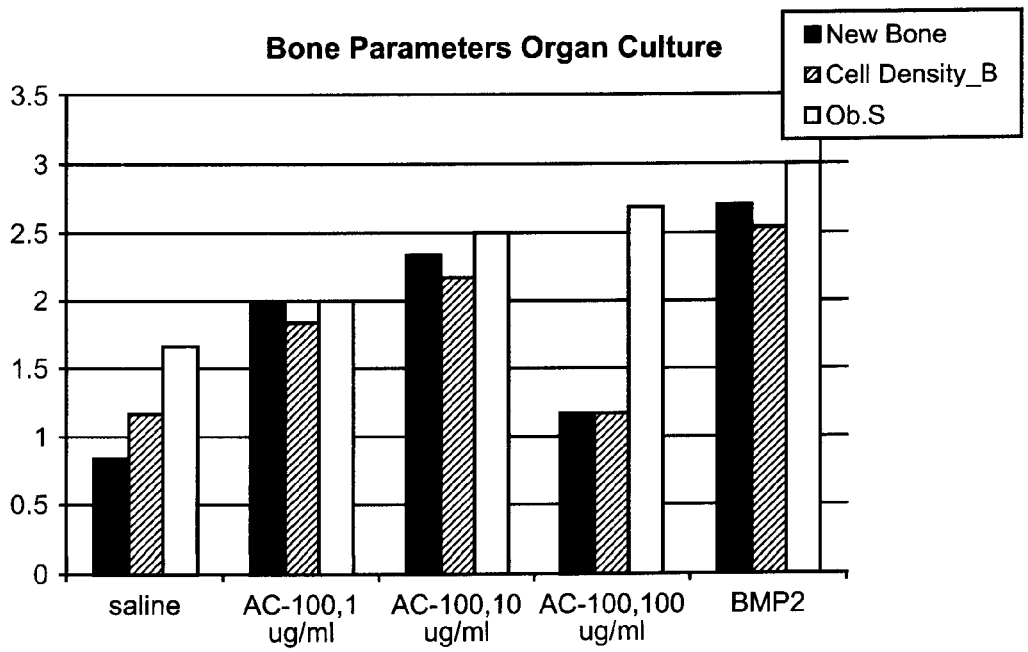
FIG. 5 is a bar graph which exhibits various bone parameters such as new bone volume, cell density in the bone tissue, and osteoblast surface in the mouse calvaria organ culture with the peptide of SEQ ID No. 8 of rhBMP-2.

Results: The groups treated with the peptide of SEQ ID NO. 8 had significant increases in PGE2 production (FIG. 4) and parameters of new bone formation, osteoblast surface and bone cell density (FIG. 5).

Discussion: These results indicate that the peptide of SEQ ID No. 8 could enhance the ability of endogenous bone factors present in the calvaria bone organ (including BMP2) to increase parameters of bone formation through an increased PGE2 production mechanism.

Example 6

Induction of the Bone Anabolic Activity of BMP-2 in Mouse Dorsal Muscle Using an Implantable Polymer Containing BMP-2 and the Peptide of SEQ ID No. 8

Materials and Methods: Polymer pellets containing both BMP-2 and the peptide of SEQ ID No. 8 in the following amounts (see table below) were implanted in the dorsal subfascia of 4 week old ICR mice. The mice were sacrificed 3 weeks later and the newly formed bones were isolated for evaluation using soft X-ray radiograph and bone mineral density determination.

|  | N = 10 | | | |
|---|---|---|---|---|
| AC-100 (µg) | 0 | 50 | 250 | 1250 |
| BMP-2 (µg) | 5 | 5 | 5 | 5 |
| BMP-2 (µg) | 3 | 3 | 3 | 3 |
| Polymer (mg) | 30 | 30 | 30 | 30 |

Figure 6:
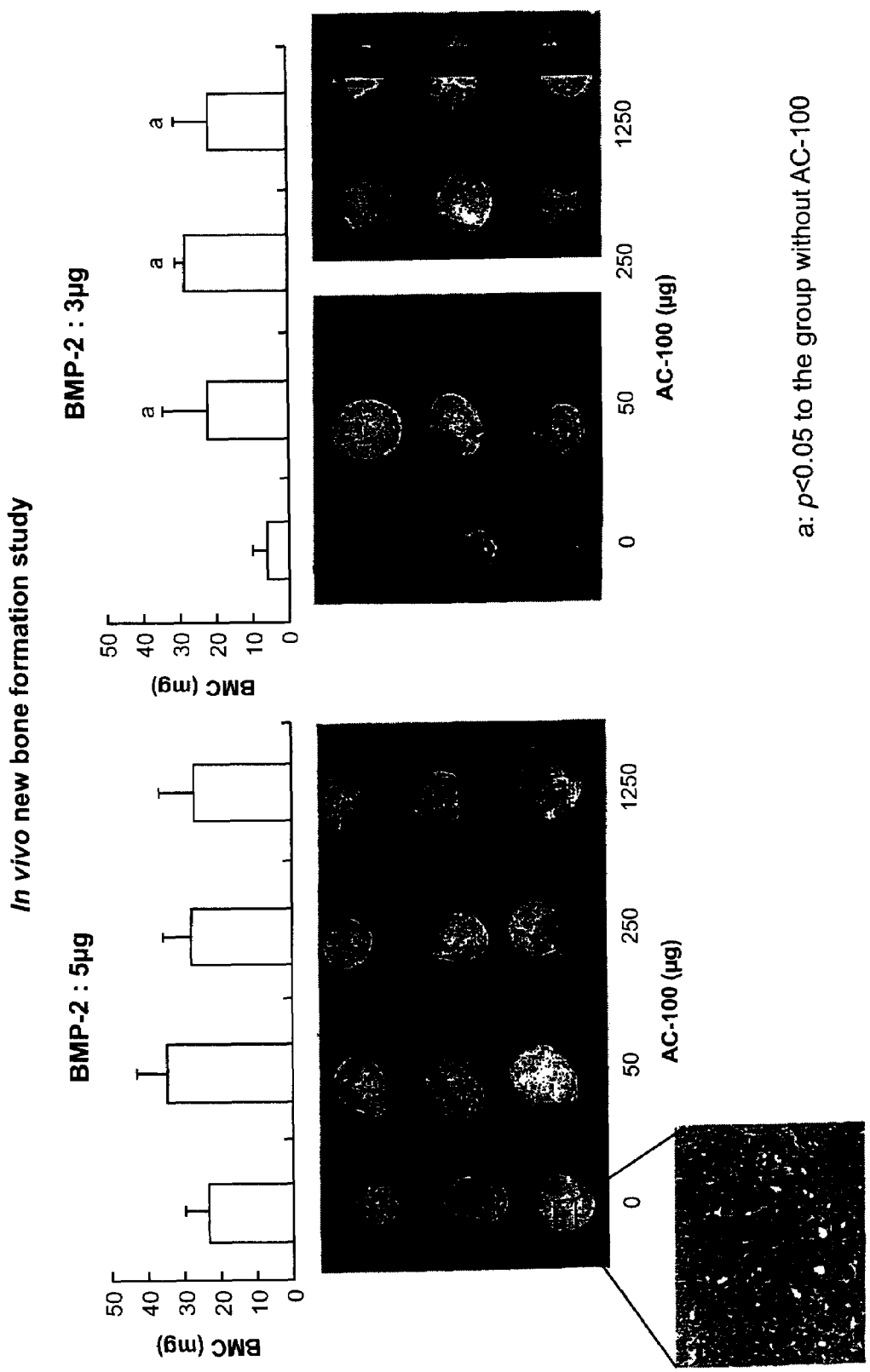
FIG. 6 shows bar graphs and images which represent radiographs (indicating new calcified tissue/bone) formed in the dorsal muscle of mice when a polymer which containing rhBMP-2 and different doses of the peptide of SEQ ID No. 8 were implanted in the tissue. (time point)

Results: As exhibited in FIG. 6, the amount of bone formation was evaluated by the size and mineral density of ectopic ossicles at three weeks after implantation of 30 mg polymer containing either 5 µg or 3 µg of BMP-2 with different doses of the peptide of SEQ ID No. 8 (0, 50, 250, or 1250 µg) into the dorsal muscle of mice (ICR). The efficacy of the peptide was unclear when 5 µg of BMP-2 was used. However, the peptide showed significant enhancement of the BMP-2 effects when 3 µg of BMP-2 was used.

Discussion: These data demonstrated that the peptide of SEQ ID No. 8 can significantly induce the bone anabolic effect of BMP-2 in vivo, especially when suboptimal doses of BMP-2 are used

| Sequence | ID |
|---|---|
| RGDBD(X)nSGZG [B, X, and Z can be any amino acid, n = 1~10]] | (SEQ ID NO.1) |
| RGDND(X)nSGZG [X and Z can be any amino acid, n = 1~10] | (SEQ ID NO.2) |
| RGDND(X)nSGDG [X can be any amino acid, n = 1~10] | (SEQ ID NO.3) |
| RGDNDJJPFSGDG [J can be any amino acid] | (SEQ ID NO:4) |
| RGDNDISPFSGDG | (SEQ ID NO.5) |
| RGDNDMSPFSGDG | (SEQ ID NO.6) |
| RGDNDVPPFSGDG | (SEQ ID NO.7) |
| TDLQERGDNDISPFSGDGQPFKD | (SEQ ID NO.8) |

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of enhancing hard tissue formation activity, comprising:
   administering to a patient an effective amount of the peptide of SEQ ID NO:8; and
   further administering to the patient an effective amount of recombinant human bone morphogenic protein-2 (rh-BMP-2);
   wherein the ratio of the rhBMP-2 to the peptide of SEQ ID NO:8 is in a range of 1:5 or more allowing the peptide and the protein to act on hard tissue forming cells and thereby enhance hard tissue formation activity.

2. The method of claim 1 wherein the hard tissue forming cells are cells chosen from the group of: (a) cells of a lineage of osteoblast wherein the hard tissue is in the form of bone tissue; (b) cells of a lineage of ameloblast wherein the hard tissue is in the form of enamel; (c) cells of a lineage of odontoblast wherein the hard tissue is in the form of dentin; and (d) cells of a lineage of cementoblast wherein the hard tissue is in the form of cementum.

3. The method of claim 1, wherein the peptide and the protein are administered by injection.

4. The method of claim 1, wherein the peptide and the protein are administered at the same time.

5. The method of claim 4, wherein the peptide and the protein are administered on an absorbable collagen sponge (ACS).

* * * * *

UNITED STATES PATENT AND TRADEMARK OFFICE
CERTIFICATE OF CORRECTION

| | | |
|---|---|---|
| PATENT NO. | : 7,638,486 B2 | Page 1 of 1 |
| APPLICATION NO. | : 11/457091 | |
| DATED | : December 29, 2009 | |
| INVENTOR(S) | : Lazarov | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 487 days.

Signed and Sealed this

Ninth Day of November, 2010

David J. Kappos
*Director of the United States Patent and Trademark Office*